US010905838B2

(12) United States Patent
Schranz et al.

(10) Patent No.: US 10,905,838 B2
(45) Date of Patent: Feb. 2, 2021

(54) VENTILATOR WITH ERROR DETECTION FOR FLOW SENSORS

(71) Applicant: Hamilton Medical AG, Bonaduz (CH)

(72) Inventors: Christoph Schranz, Bonaduz (CH); Karolin Franke, Chur (CH); Dominik Novotni, Chur (CH)

(73) Assignee: Hamilton Medical AG, Bonaduz (CH)

( * ) Notice: Subject to any disclaimer, the term of this patent is extended or adjusted under 35 U.S.C. 154(b) by 380 days.

(21) Appl. No.: 15/757,208

(22) PCT Filed: Sep. 1, 2016

(86) PCT No.: PCT/EP2016/070572
§ 371 (c)(1),
(2) Date: Mar. 2, 2018

(87) PCT Pub. No.: WO2017/037152
PCT Pub. Date: Mar. 9, 2017

(65) Prior Publication Data
US 2019/0192796 A1 Jun. 27, 2019

(30) Foreign Application Priority Data
Sep. 3, 2015 (DE) .................. 10 2015 216 895

(51) Int. Cl.
*A61M 16/00* (2006.01)
*A61M 16/20* (2006.01)
(Continued)

(52) U.S. Cl.
CPC .... *A61M 16/0051* (2013.01); *A61M 16/0057* (2013.01); *A61M 16/0066* (2013.01);
(Continued)

(58) Field of Classification Search
CPC ....... A61B 5/0205; A61B 5/024; A61B 5/087; A61B 5/091; A61B 5/14542;
(Continued)

(56) References Cited

U.S. PATENT DOCUMENTS 5,704,345 A * 1/1998 Berthon-Jones ....... A61B 5/087
128/204.23
7,044,129 B1 * 5/2006 Truschel ............... A61M 16/12
128/204.18

(Continued)

FOREIGN PATENT DOCUMENTS

AU 2002360922 9/2003
CN 103432671 A 11/2012
(Continued)

OTHER PUBLICATIONS

International Search Report Issued in PCT/EP2016/070572.
(Continued)

*Primary Examiner* — Annette Dixon
(74) *Attorney, Agent, or Firm* — Prince Lobel Tye LLP (57) ABSTRACT

The present artificial respiration ventilator (10) comprises, inter alia, a flow sensor arrangement (44, 48) for quantitatively detecting a gas flow in a breathing line arrangement (30), comprising a distal flow sensor (48) located farther from the patient end of the ventilation line arrangement (30), and a proximal flow sensor (44) located closer to the patient end of the ventilation line arrangement (30), and has a control device (18) at least for processing measurement signals of the flow sensor arrangement (44, 48), wherein the control device (18) is designed for error detection based on the measurement signals of the distal (48) and/or the proximal sensor (44). According to the invention, the control device (18) is designed to detect an error of the flow sensor arrangement (44, 48) on the basis of a comparison of a change value (62, 76) of a measurement signal (54, 58, 68,
(Continued)

72) of the one flow sensor (44) with a change value (60, 74) of a measurement signal (52, 56, 66, 70) of the respective other flow sensor (48) or/and with a measurement signal (54, 58, 68, 72) of the one flow sensor (44).

31 Claims, 7 Drawing Sheets

(51) Int. Cl.
  *A61M 16/04* (2006.01)
  *A61M 16/08* (2006.01)
  *A61M 16/14* (2006.01)
  *A61M 16/16* (2006.01)

(52) U.S. Cl.
  CPC ...... *A61M 16/024* (2017.08); *A61M 16/0463* (2013.01); *A61M 16/0858* (2014.02); *A61M 16/14* (2013.01); *A61M 16/204* (2014.02); *A61M 16/205* (2014.02); *A61M 16/16* (2013.01); *A61M 16/162* (2013.01); *A61M 2016/0027* (2013.01); *A61M 2016/0036* (2013.01); *A61M 2205/18* (2013.01)

(58) Field of Classification Search
  CPC ........ A61B 5/7257; A61F 5/56; A61M 16/00; A61M 16/0003; A61M 16/0006; A61M 16/0051; A61M 16/0066; A61M 16/0069; A61M 16/0096; A61M 16/024; A61M 16/026; A61M 16/04; A61M 16/0666; A61M 16/0688; A61M 16/0825; A61M 16/0833; A61M 16/0841; A61M 16/085; A61M 16/0858; A61M 16/1005; A61M 16/105; A61M 16/107; A61M 16/709; A61M 16/1095; A61M 16/12; A61M 16/16; A61M 16/161; A61M 16/162; A61M 16/20; A61M 16/202; A61M 16/203; A61M 16/204; A61M 16/209; A61M 2016/0021; A61M 2016/0027; A61M 2016/003; A61M 2016/0033; A61M 2016/0036; A61M 2016/0039; A61M 2016/0042; A61M 2016/1025; A61M 2202/0208; A61M 2202/0225; A61M 2205/15; A61M 2205/18; A61M 2205/3303; A61M 2205/3334; A61M 2205/3348; A61M 2205/3355; A61M 2205/3358; A61M 2205/3368; A61M 2205/3375; A61M 2205/3379; A61M 2005/3561; A61M 2205/3569; A61M 2205/3592; A61M 2205/502; A61M 2205/505; A61M 2205/52; A61M 2205/581; A61M 2205/582; A61M 2205/75; A61M 2205/8206; A61M 2205/8237; A61M 2209/084; A61M 2230/005; A61M 2230/04; A61M 2230/06; A61M 2230/10; A61M 2230/202; A61M 2230/205; A61M 2230/42; A61M 2230/432; A61M 2230/435; A61M 2230/60; A61M 2230/63; A61M 2240/00; Y02A 90/22; Y02A 90/26

See application file for complete search history.

(56) References Cited

U.S. PATENT DOCUMENTS

| | | | |
|---|---|---|---|
| 7,115,097 B2* | 10/2006 | Johnson | A61M 16/024 600/538 |
| 8,528,552 B2* | 9/2013 | von Blumenthal | A61M 16/0051 128/204.21 |
| 9,259,545 B2* | 2/2016 | Heesch | A61M 16/00 |
| 9,999,742 B2* | 6/2018 | Millar | A61M 16/209 |
| 10,279,133 B2* | 5/2019 | Heesch | A61M 16/0081 |
| 10,350,379 B2* | 7/2019 | Sweeney | A61M 16/0069 |
| 2007/0062533 A1* | 3/2007 | Choncholas | A61M 16/024 128/204.23 |
| 2007/0157930 A1 | 7/2007 | Soliman et al. | |
| 2008/0257350 A1 | 10/2008 | Huang et al. | |
| 2009/0272381 A1 | 11/2009 | Dellaca et al. | |
| 2011/0265793 A1* | 11/2011 | Haveri | A61M 16/085 128/204.22 |
| 2016/0193438 A1* | 7/2016 | White | A61M 16/0003 128/203.12 |
| 2018/0104426 A1* | 4/2018 | Oldfield | A61B 5/091 |

FOREIGN PATENT DOCUMENTS

| | | |
|---|---|---|
| JP | H09173456 A | 7/1997 |
| JP | H10503675 A | 4/1998 |
| JP | 2001245984 A | 9/2001 |
| JP | 2006507905 A | 3/2006 |
| JP | 2010501289 A | 1/2010 |
| JP | 2011038793 A | 2/2011 |
| WO | WO 03/055552 | 7/2003 |
| WO | 2009/119449 A1 | 10/2009 |

OTHER PUBLICATIONS

International Preliminary Report on Patentability issued in PCT/EP2016/070572.
Chinese Office Action issued in CN 201680051327.9 dated Dec. 26, 2019.
Japanese Office Action issued in JP 2018-511656 dated Mar. 30, 2020.

* cited by examiner

VENTILATOR WITH ERROR DETECTION FOR FLOW SENSORS

CROSS REFERENCE TO RELATED APPLICATIONS

This application is the National Stage of International Application No. PCT/EP2016/070572, filed on Sep. 1, 2016, which claims priority to German Application No. 10 2015 216 895.6, filed on Sep. 3, 2015. The contents of both applications are hereby incorporated by reference in their entirety.

BACKGROUND

Field of the Invention

The present invention relates to a ventilation device for artificial respiration with
- a breathing gas source,
- a ventilation duct arrangement extending between the breathing gas source and a patient-side, proximal end,
- a valve assembly comprising an inspiratory valve and an expiratory valve,
- a flow sensor arrangement for quantitatively detecting a gas flow in the ventilation line arrangement, comprising a distal flow sensor located farther from the patient end of the ventilation line arrangement and a proximal flow sensor located closer to the patient end of the ventilation line arrangement, and
- a control device at least for processing measurement signals of the flow sensor arrangement, wherein the control device is adapted to close based on measurement signals of the distal and/or the proximal sensor to an error.

Description of the Related Art

Such a ventilation device is known, for example, in the market as the product "SERVO-U" from Maquet. This known ventilation device uses an internal sensor inside a ventilator as a distal flow sensor. The ventilator has the distal end of the breathing line—connected. Furthermore, the known ventilator uses a proximal flow sensor in the form of a hot wire anemometer in a Y-connector, in which towards the patient towards an inspiratory and an expiratory breathing tube are connected to a common ventilation line leading to the patient's ventilation line. The instruction manual for this known ventilator indicates that the outputs of internal pressure and flow sensors are compared with the measurement result of the proximal sensor in the Y-connector and the proximal sensor will be deactivated if a significant deviation is determined between the values used for comparison.

A disadvantage of the known ventilation device and the error detection disclosed therein is that the mere detection of errors based on a comparison of measured values of two different sensors is only able to detect a part of the sensor errors actually occurring at the sensor arrangement. Additionally, between both sensors, the ventilation line arrangement is placed in the form of an elastic tube, which is stretched at each breath by the breathing gas flowing through it against its elasticity. Due to this tube elasticity, the two flow sensors arranged at different points in the breathing gas flow deliver different measured values at both detection points even with the same effective breathing gas flow. The breathing gas expanding the tube passes through the distal flow sensor, but not the proximal flow sensor, and thus the measured values of the distal flow sensor are usually higher than those of the proximal one.

Ventilation devices are life-saving devices for patients who cannot breathe autonomously or inadequately. Their correct function is therefore crucial. The correct function of the respiratory devices in turn depends on the most accurate possible detection of the amount of breathing gas supplied to a patient.

SUMMARY OF THE INVENTION

It is therefore an object of the present invention to develop a ventilation device of the type mentioned in such a way that any malfunction of the flow sensor arrangement can be reliably detected early.

This object is achieved according to the invention by a generic ventilator in which the control device is designed to detect an error of the flow sensor arrangement based on a comparison of a change value of a measurement signal of one flow sensor from the proximal and distal flow sensor with a change value of a measurement signal of the other flow sensor from either the proximal or distal flow sensor. By using change values of the measurement signal instead of the measurement signal itself, errors of the flow sensor arrangement can be detected earlier or/and more reliably than before. Thus, it is possible, for example, to already detect an error if the measured values of the proximal and distal flow sensors change only very slightly, but in different directions, for example one flow sensor indicates an increase in the flow rate and the other flow sensor a reduction. Thus, an error can already be detected, although a comparison of the measured values of the two flow sensors would not yet show any significant deviation from one another.

Alternatively or additionally, the change value of the measurement signal of the one flow sensor from the proximal and distal flow sensor can be compared with a measurement signal of the same flow sensor, i.e. once again of the one flow sensor, so that solely on the basis of signals from one and the same flow sensor: either the proximal or distal flow sensor, without taking into account the signals of the other flow sensor can detect a fault of a flow sensor, such as when its change value based on the last measurement signal before the change due to the prevailing operating conditions is unusually large or unusually small.

When comparing change values of different sensors with each other, these are simultaneous or quasi-simultaneous change values, i.e. change values which are determined at the same time or during the same breath.

If a change value of a measurement signal is compared with a measurement signal, this is a comparison of a change value with a measurement signal detected earlier in time, preferably with a measurement signal determined immediately before the change value.

The present invention-proposed solution therefore allows to detect errors to a greater extent than was known for respiratory devices of the prior art and also allows to detect errors of a flow sensor independently of signals from another flow sensor.

A particularly reliable error detection can be obtained if the above possibilities for detecting errors in the flow sensor arrangement are applied not only alternatively but cumulatively.

As already indicated above, rapid and effective error detection is possible if the control device is designed to detect an error in the flow sensor arrangement if the change value of the measurement signal of the one flow sensor from the distal and proximal flow sensor has an opposite direction of change than the change value of the other flow sensor. Furthermore not even numerical values must be compared with each other, but a comparison of the signs of the respective change values with one another may be sufficient to conclude an error.

At the flow sensor arrangement, in particular at the proximal flow sensor, essentially two different types of errors occur according to experiences so far, which differ mainly by the length of time in which they develop and have an effect on the ventilation device.

The one error, which is referred to as "jump error" in the following, occurs suddenly and leads to a considerable error in the measurement result within a few seconds.

The other error, hereafter referred to as "drift error", creeps up and develops over several minutes, up to half an hour or three quarters of an hour, in to a considerable error in the measurement result.

According to previous findings these two errors are most likely related to the precipitation of condensate in the proximal flow sensor. The fact that the proximal flow sensor is located very close to the patient, means it can be more influenced by moisture in the breathed air. While the jump errors are very well understood, especially with flow sensors that operate on the differential pressure principle, for the drift error it has so far has been only phenomenologically observed that it disappears when a condensed flow sensor has been replaced by a dry one after having recognized the drift error.

Although at least the proximal flow sensor preferably works according to the differential pressure principle, as is known for example from DE 10 2010 040287 A1, the present invention should not be limited to ventilation devices with a flow sensor arrangement with at least one pressure differential principle based flow sensor. The presently proposed improved ventilation device with increased accuracy in error detection in flow sensors can basically use any flow sensor, regardless of which physical principles it uses to measure the gas flow.

For the sake of completeness, it should be mentioned that, according to current theory, the jump error occurs in a proximal flow sensor according to DE 10 2010 040287 A1 which operates according to the differential pressure principle when a movable flap which separates two pressure measuring chambers arranged consecutively in the flow direction of the sensor, is immersed in collected condensate within the sensor and therefore must overcome greater resistance for motion than in a dry sensor.

The jump error may then be advantageously detected quickly and reliably if the control device is designed to detect an error of the flow sensor arrangement, if
  a ratio of a sum value of consecutively occurring change values of the measurement signal of the proximal flow sensor to a first reference value exceeds a predetermined reference threshold value, and
  when a ratio of a sum value of consecutively occurring change values of the measurement signal of the distal flow sensor to a second reference value falls below a predetermined reference threshold value.

In this case, sequentially occurring change values of the measurement signal of the proximal and the distal flow sensor are summed in order to quantify the total change of the measurement signal of the respective flow sensor occurring over the duration of the summation. This sum of change in the measured signal may then be related to a reference value to judge whether or not the flow sensor arrangement is operating properly. The assessment may be based on a predetermined reference threshold.

In order to form the summation value, change values of measurement signals adding immediately after one another are preferably accumulated in order to be able to form the summation value over as short a period as possible and to be able to quickly determine a corresponding error in the flow sensor arrangement. In addition, it is thus possible to ensure that no change value of a measuring signal is disregarded for the purpose of ensuring the correctness of the operation of the flow sensor arrangement.

According to a preferred development of the present invention, the first or/and the second reference value is a measured signal value of the proximal flow sensors. Thereby, the change values of the proximal flow sensor and the change values of the distal flow sensor may each be related to a sum of the changes of the proximal flow sensor as the more error-prone flow sensor between the proximal and distal flow sensors. This is often helpful for the assessment of the correct operation of the flow sensor arrangement, since the absolute value of a change of a measuring signal in terms of its plausibility is usually only reasonable judgable in connection with the measured value which is changed by the change. Accordingly, the accuracy of the error detection, in particular a jump error, can be increased by the fact that the first or/and the second reference variable is a measurement signal value of the proximal flow sensor at or immediately before the beginning of the summation of the change values. Then, the changes are directly related to the measurement signal with which they are used to assess their plausibility or correctness.

However, the ventilator is not required to permanently perform error detection during its entire operation. It is sufficient to provide the computing power of the control device of the ventilator for more accurate error detection when this need emerges during the operation of the ventilation device.

Preferably, therefore, the control device of the ventilation device is designed to permanently monitor the operation of the flow sensor arrangement for faults according to a first, less computationally demanding test method, and is further adapted to the operation of the flow sensor arrangement when the first test method indicates a suspected fault condition of the flow sensor arrangement to monitor for errors according to a second, more computationally demanding test method.

For the preferred case of an intensive test method already described above, this may mean that the control device is designed to start summing change values if the measurement signal value and/or the change value of the proximal flow sensor exceeds a predetermined signal threshold value. The check, as to whether the measured signal value and/or the change value of the proximal flow sensor exceeds a predetermined signal threshold value is preferably carried out permanently and corresponds to the first test method which is described above in abstract, which requires less computing power. Then, when the change value or/and the measurement signal value of the proximal flow sensor exceeds the predetermined signal threshold, a suspected fault condition is determined, so that preferably the summation of change values described above and their comparison with reference values are initiated.

In parallel, the first test procedure may be continued and it may be considered to terminate the second test procedure if the first test procedure no longer indicates a suspected fault condition over a predetermined number of breathing cycles, i.e., for example, the measurement signal value and/or the change value of the proximal flow sensor no longer exceeds a predetermined absolute value threshold value of consecutively evaluated measurement signals.

However, it may also be considered to continue the second, more computationally-demanding test procedure until the ventilator device has ceased operation once a suspected fault condition has been determined.

In a preferred configuration of the ventilation device, the distal flow sensor can serve for the most accurate control of the flow of breathing gas during a breath. This means that the flow of breathing gas is changed during a breath based on the measurement signal provided by the distal flow sensor.

In contrast, the proximal flow sensor can be used to control the minute ventilation, as it is used for example in the known ventilation modes ASV, Intellivent-ASV and APV. In this case, the minute ventilation is preferably set or regulated only by breath, i.e. there is no change in the breathing gas flow during the breath stroke on the basis of the measurement signal of the proximal flow sensor. This has the advantage that the breathing gas volume actually administered to the patient can be determined more accurately with the proximal flow sensor located closer to the patient than with the distal flow sensor, inter alia because of the negative influencing effects on the accuracy of the measurement signal, such as the elasticity of tubing in the breathing tube, do not affect the measurement signal of the proximal flow sensor or only to a very limited extent.

Due to the arrangement of the distal and the proximal flow sensor, the distal flow sensor is preferably perfused exclusively with inspiratory breathing gas, while the proximal flow sensor is perfused with both inspiratory and expiratory breathing gas. This also results in an increased susceptibility to errors of the proximal flow sensor compared to that of the distal flow sensor.

Since the ventilation device, although it changes breathing gas flows during a breath as described above, substantially ventilates the patient with discrete breaths, it may preferably be considered that the control device is adapted to process the measurement signals of the proximal and distal flow sensor on a by breath basis. This has the advantage that most respiratory parameters which determine the operation of the ventilator are available on a by breath manner, i.e. to be executed on the respective respiratory breath.

In this case, with a preferred evolved configuration, to further increase the accuracy of the fault detection when the measured signal value of the proximal flow sensor exceeds the predetermined absolute value threshold value at a threshold breath, the first and/or second reference value is the measurement signal value of the proximal flow sensor which is associated with the threshold breath immediately preceding that breath. This in turn, also serves to produce as immediate as possible a temporal relationship between the measuring signals or/and change values to be used for the error detection of the flow sensor arrangement and the reference value with which the signals or values are related.

Experiments have shown that the drift error can be well detected by the fact that the control device is designed to detect an error of the flow sensor arrangement, when a ratio of a sum value of consecutively occurring, preferably immediately successive, change values of the measurement signal of the proximal flow sensor to a third reference variable exceeds a predetermined reference threshold value, and when a ratio of a sum value of consecutively occurring, preferably immediately successive, change values of the measuring signal of the distal flow sensor to a fourth reference variable falls below a predetermined reference threshold value, or to detect an error in the flow sensor arrangement when a ratio of a sum value of consecutively occurring, preferably immediately successive, change values of the measurement signal of the proximal flow sensor to a fifth reference variable falls below a predetermined reference threshold value and a ratio of a sum value of consecutively occurring, preferably immediately successive, change values of the measurement signal of the distal flow sensor to a sixth reference value exceeds a predetermined reference threshold value.

It should be noted at this point that the use of ordinal numbers to distinguish the reference thresholds in the present application reflects the order in which the reference thresholds are entered in the notification text and should not be taken as indicating a minimum number of reference thresholds in the ventilator.

The advantages of using immediately successive change values is shown in the above statements for the determination of the jump error, which also apply here. The above reference threshold values can be determined by experiments taking into account medical edge conditions without significant effort.

In principle, the drift error can already be reliably determined with the conditions mentioned above. An even higher detection accuracy of the drift error can be achieved with the control device designed to only detect an error of the flow sensor arrangement, if additionally the sum value of consecutively occurring, preferably immediately successive, change values of the measurement signal of the proximal flow sensor exceeds a predetermined first sum threshold value, or/and the sum value of consecutively occurring, preferably immediately successive, change values of the measurement signal of the distal flow sensor exceeds a predetermined second sum threshold value.

Again, the cumulative application of the above conditions increases the accuracy. The summation preferably occurs for both sensors from a common beginning to the current breath.

In principle, any suitable reference values for the evaluation of the plausibility or correctness of change values of the measurement signal of one of the two or both flow sensors can be used. As already explained above, a particularly meaningful reference variable for evaluating changes in the measurement signals or of the measurement signals themselves is a measurement signal value of the proximal flow sensor. Therefore, according to an advantageous evolution—of the present invention, the third and/or the fifth reference variable is a measured signal value of the proximal flow sensor. In order to establish as close as possible a relationship between the reference variable and the variables to be assessed, the third or/and the fifth reference variable is preferably a measured signal value of the proximal flow sensor at or immediately before the beginning of the summation of the change values.

In the same vein, a preferable development of the present invention would foresee that the fourth and/or the sixth reference variable is a measurement signal value of the distal flow sensor, in particular a measurement signal value of the distal flow sensor at or immediately before the beginning of the summation of the change values.

Here too it can be foreseen that the summation of change values for the formation of summation values begins when the absolute value of the change value of the measurement signal of the proximal and/or the distal flow sensor exceeds an absolute value.

In this case, in turn, the comparison of the absolute value of the change value of the measurement signal of the proximal and/or distal flow sensor with an absolute value is a first, less computationally demanding test method in the above sense, from which the above-described second, more computationally demanding test method can be triggered. Out clearly the duration of the execution of more processing power requiring investigation to determine the drift error referred to above, to determine a jump error, which also are present in connection with the determination of the drift error.

A first test method for determining whether a second test method requiring more computing power should be started may alternatively or additionally be a comparison of the direction of change, that is to say the signs, of change values of the proximal and distal flow sensors of the same breath. If the signs are different, i.e. if the measurement signals from the proximal and distal flow sensors change in different directions for the same breath, then there is sufficient suspicion of error to initiate the second test procedure.

In order not to include disruptive effects as far as possible in the consideration of the variables used for error detection, the control device can be designed to smooth the measurement signals of the flow sensors by filtering. A disruptive effect can be, for example, the spontaneous respiratory activity of a patient equipped with a ventilator.

One possible type of effective filtering is moving averaging. Since the jump error occurs quickly, i.e. within a few seconds, it suffices to form the moving average over a few change values or/and the measured signal value, for example over not more than 25, preferably not more than 20, and ideally example over 16 values, Preferably, a moving weighted average may be formed to differentiate breaths occurring at different times. For example, it may be useful to take into account the values that preceded the current measurement less strongly than those that lagged further in time when taking into account the moving average. Likewise, it can also have a positive effect on the accuracy of the error detection, if the values to be filtered at the end of the time window considered for the filtering are again weighted less than, for example, those considered for filtering from the middle of the time window.

Also for the determination of the drift error, the measured signal values of the two flow sensors can each be smoothed by a moving average, in particular by a weighted moving average.

Additionally, or alternatively, the measured signal values to be smoothed can also be filtered by a digital filter with a higher order than 1, whereby even better smoothing effects without loss of precision in error detection can be achieved by filtering with an order higher than 2, more preferably with a fourth-order digital filter. Such a digital filter is preferably used in the determination of the drift error.

Since the drift error occurs over a longer period of several minutes, a larger number of measurement signals are preferably included in the smoothing of the measurement signals by an optionally weighted moving average or by the digital filter than in the case of smoothing for the determination of the jump error. Preferably, for smoothing to determine the drift error, at least the last 50 measured values, preferably at least the last 75 measured values, and most preferably at least the last 100 measured values are used.

The control device is then preferably designed to determine the change values on the basis of the smoothed measurement signals.

It should be made clear at this point that a first-order digital filter is understood to mean a recursive filter specification using a filter coefficient a in accordance with the following structure:

$$y(n)=a\times y(n-1)+(1-a)\times x(n)$$

where y (n) is the filter output for the nth breath, y (n−1) is the filter output for the immediately preceding (n−1)-th breath, and x (n) is the current input signal for the nth breath is. a is a filter coefficient determined for the filter.

An m-order filter is the m-fold application of the above-mentioned filter structure with the i-th order filter output for the nth breath as the input signal of the next higher (i+1)-th order filter for the nth Breath, where $1 \leq i < m$.

Preferably, the proximal and the distal flow sensor do not operate continuously, but time-discretely, so that the proximal and the distal flow sensor each deliver one, preferably exactly one, measured value per breath, which represents the gas flow associated with this breath.

In order not only to detect an error, but also to be able to derive measures in the event of an error detection, the control device is preferably designed to output an alarm when it detects an error. Unlike the prior art, however, it is not necessary to deactivate a sensor—. Therefore, the control device is preferably designed to continue the processing of measurement signals of the proximal flow sensor and in particular to continue to check for the presence of a sensor error.

BRIEF DESCRIPTION OF THE DRAWING FIGURES

The present invention will be explained in more detail with reference to the accompanying drawings. It shows.

DETAILED DESCRIPTION OF THE PREFERRED EMBODIMENTS

Figure 1:
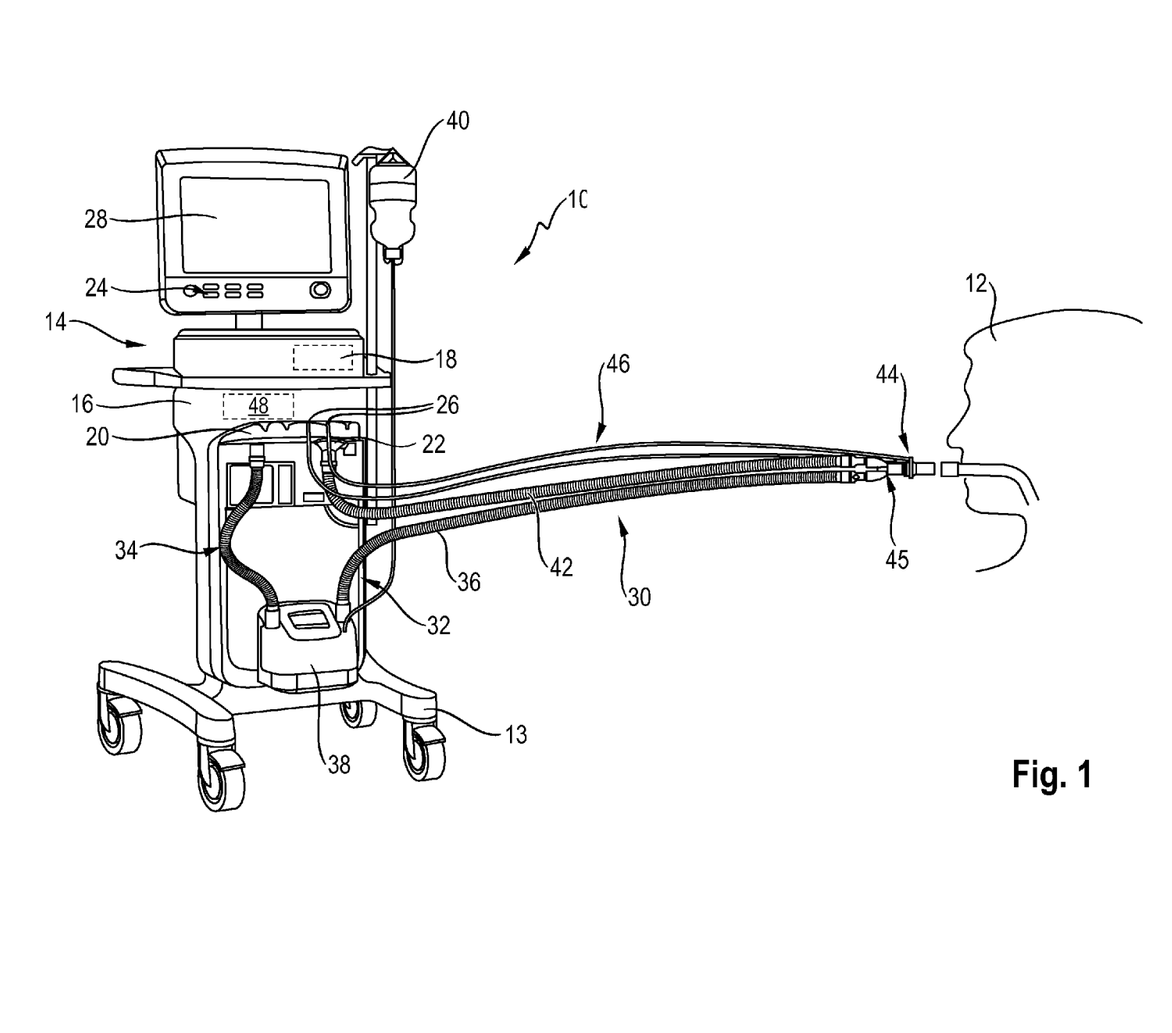
FIG. 1 shows a configuration according to the invention of a ventilator of the present invention.

In FIG. 1, a configuration of a ventilator according to the invention is designated generally by 10. The ventilator 10 is used in the illustrated case of artificial respiration of a human patient 12.

For the sake of completeness, it should be pointed out that the ventilator 10 according to the invention can be accommodated as a mobile device on a rollable frame 13.

The ventilator 10 has a housing 14 in which—not visible from the outside because of the opaque housing material—a pressure change arrangement 16 and a control device 18 can be accommodated.

The pressure change arrangement 16 is constructed in per se known and may include a pump, a compressor, a fan, a pressure vessel, a reducing valve and the like. Next, the ventilator 10 in known per se features an inspiration valve 20 and an expiratory valve 22.

The control device 18 is usually realized as a computer or microprocessor. It comprises a memory device (not shown in FIG. 1) in order to store and if required call the necessary data for the operation of the ventilator 10. The memory device can also be located outside of the housing 14 during network operation and via a data transmission connection be connected to the control device 18. The data transmission connection may be formed by a cable or a radio link. However, in order to prevent disturbances of the data transmission connection from affecting the operation of the ventilator 10, the memory device is preferably integrated in the control device 18 or accommodated at least in the same housing 14 as this.

To input data into the ventilator 10 or more precisely into the control device 18, the ventilator 10 has a data input 24, which is represented in the example shown in FIG. 1 by a keyboard. As an alternative or in addition to the illustrated keyboard, the control device 18 may receive data via various data inputs, for example via a network link, a radio link or via sensor connections 26, which will be discussed in more detail below.

To output data to the treating therapist, the ventilator 10 may include an output device 28, as shown as a screen in the example.

For artificial respiration, the patient 12 is connected to the ventilator 10, more precisely to the pressure change arrangement 16 in the housing 14, via a ventilation line arrangement 30. The patient 12 is intubated for this purpose.

The ventilation line arrangement 30 has an inspiratory tube 32, via which fresh breathing gas can be conducted from the pressure change arrangement 16 into the lungs of the patient 12. The inspiratory tube 32 may be interrupted and have a first inspiratory part tube 34 and a second inspiratory part hose 36, between which a conditioning device 38 may be fitted for targeted humidification and optionally also temperature of the fresh breathing gas supplied to the patient 12. The conditioning device 38 may be connected to an external fluid reservoir 40, via which water for humidification or a drug, such as anti-inflammatory or to expand the airway, can be supplied to the breathing gas. For use of the present ventilator 10 as an anesthesia ventilation device so volatile anesthetics can be delivered controlled via the ventilator 10 to the patient 12. The conditioning device 38 ensures that the fresh breathing gas is fed to the patient 12 with a predetermined moisture content, optionally with the addition of a drug aerosol and at a predetermined temperature.

The ventilation line arrangement 30 has, in addition to the already mentioned inspiratory valve 20, an expiratory valve 22 and a further expiratory tube 42 via which metabolized breathing gas is released from the lungs of the patient 12 into the atmosphere.

The inspiratory tube 32 is coupled to the inspiratory valve 20, the expiratory tube 42 with the expiratory valve 22. Of the two valves only one is open at the same time for the purpose of gas flow. The actuation control of the valves 20 and 22 is also carried out by the control device 18.

During a ventilation cycle, the expiratory valve 22 is initially closed for the duration of the inspiration phase and the inspiratory valve 20 is opened so that fresh breathing gas can be conducted from the housing 14 to the patient 12. A flow of the fresh breathing gas is effected by targeted pressure increase of the breathing gas by the pressure change arrangement 16. Due to the increase in pressure, the fresh breathing gas flows into the lungs of the patient 12 and expands the body area near the lungs there, i.e. in particular the thorax, against the individual elasticity of the body parts in proximity of the lungs. As a result, the gas pressure inside the lung of the patient 12 also increases.

At the end of the inspiration phase, the inspiratory valve 20 is closed and the expiratory valve 22 is opened. Then the expiratory phase begins. Due to the increased gas pressure of the breathing gas in the lungs of patient 12 until the end of the inspiratory phase, this flows into the atmosphere after opening the expiratory valve 22, with decreasing gas pressure in the lungs of the patient 12 as flow duration increases. When the gas pressure in the lung of patient 12 reaches the positive end-expiratory pressure set at ventilator 10, i.e. a slightly higher pressure than the atmospheric pressure, the expiratory phase is terminated with the closing of the expiratory valve 22 and it is followed by another ventilation cycle.

During the inspiration phase, the patient 12 is supplied with the so-called respiratory tidal volume, i.e. the breathing gas volume per breath. The ventilation tidal volume multiplied by the number of ventilation cycles per minute, i.e., multiplied by the ventilation frequency, gives the minute volume of the artificial ventilation presently performed.

Preferably, the ventilator 10, in particular the control device 18, is designed to repeatedly update or determine respiratory operating parameters that characterize the ventilation mode of the ventilator 10 during the ventilation operation, in order to ensure that the ventilation mode optimally optimizes the ventilation at any time for each patient 12 to be respirated. Particularly advantageous is the determination of one or more ventilation operating parameters with the ventilation frequency, so for each ventilation cycle the current and thus optimally adapted ventilation operating parameters can be provided to the patient 12.

For this purpose, the ventilator 10 can be connected for data transmission with one or more sensors which monitor the condition of the patient and/or the operation of the respiration device.

One of these sensors is a proximal flow sensor 44, which detects the breathing gas flow prevailing there in the ventilation line arrangement 30 via a Y connection piece 45. The proximal flow sensor 44 can, by means of a sensor line-arrangement 46, be coupled to the data inputs via sensor connections 26 of the control device 18. The sensor line assembly 46 may include, but is not limited to, electrical signal transmission lines. It may also have hose lines which transmit the gas pressure prevailing in the flow direction on both sides of the proximal flow sensor 44 to the data inputs via sensor connections 26, where these are quantified by pressure sensors not shown in FIG. 1. The proximal flow sensor 44 is present as a differential—pressure flow sensor. Although the flow sensor 44 is preferably a flow sensor operating according to the differential pressure principle, it can also be a flow sensor operating according to another physical operating principle.

In housing 14, a further distal flow sensor 48 is provided, which is referred to as a distal flow sensor 48 due to its greater distance from the patient 12—compared with the proximal flow sensor 44.

The distal flow sensor 48 and its measurement signal can, for example, control the flow of breathing gas during an inspiratory phase through the ventilation line assembly 30, in the case of the distal flow sensor 48 more accurately by inspiratory tube 32, while the proximal flow sensor 44 and its measurement signal control the supplied minute volume of patient 12. The distal flow sensor 48 therefore preferably has a faster response than the proximal flow sensor 44, since the measurement signal of the distal flow sensor 48 also serves to change the flow of breathing gas during a breath, while the measurement signal of the proximal flow sensor 44 is preferably considered only on each breath, thus on which no change in the flow of breathing gas through the Y-connector 45 during a breath occurs.

Because of its location in the Y-connector 45, the proximal flow sensor 44, in contrast to the distal flow sensor 48, is also basically capable of sensing the flow of expiratory breathing gas through the expiratory tube 42.

The proper function of the proximal flow sensor 44 and distal flow sensor 48 is essential to the proper operation of the ventilator 10, and thus to the health of the patient 12.

It has been shown in operation that the proximal flow sensor 44 due to its proximity to the patient 12 is subject to a greater risk of error than the distal flow sensor 48. The proximal flow sensor 44 through which also expiratory breathing gas flows, is more affected by moisture contained in the breathing gas, for example, than the distal flow sensor 48. This is all the more true if the distal flow sensor 48 is arranged in inspiration direction as in the present example of FIG. 1 upstream of the conditioning device 38 and thus is only substantially flowed through by dry inspiratory breathing gas.

The control device 18 of the ventilator 10 according to the invention is designed to monitor the operation of the flow sensor arrangement formed by the proximal flow sensor 44 and the distal flow sensor 48 in order to recognize a malfunction of the flow sensor arrangement in good time.

According to the experiences made so far, two types of errors which differ with regard to the speed of their occurrence occur at the proximal flow sensor 44, namely a jump error occurring rapidly within a few seconds and a drift error which occurs creepingly within several minutes.

The detection of the jump error will be described first.

Figure 2:
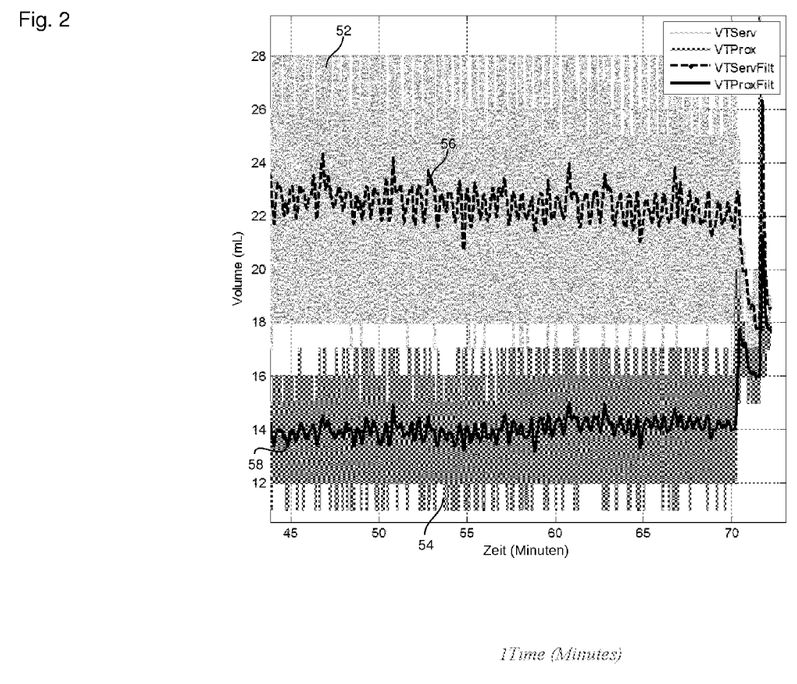
FIG. 2 shows a diagram with raw measurement signals and smoothed measurement signals of the distal and the proximal flow sensor.

In FIG. 2, the detection signals of the proximal flow sensor 44 are shown as "VTProx" with reference number 52 and the distal flow sensor 48 as "VTServ" with reference number 54. These are time-discrete signals in their form as detected directly by the respective proximal flow sensor[[s]] 44 and distal flow sensor 48.

In principle, these signals can be used to carry out the error detection according to the invention. To increase the reliability of detection of errors, in particular at the proximal flow sensor 44, it is recommended, however, to smooth these signals.

For the detection of the spontaneously occurring jump error, a smoothing method is advantageous, which takes into account only a few measuring signals and thus does not suppress short-term changes in the sensor signals. The smoothing has proved to be advantageous for this purpose through the formation of a weighted moving average, for example over the last 16 measured values. The measurement signals of the proximal flow sensor 44 and the distal flow sensor 48 are advantageously smoothed with the same measurement method and the same filter coefficients. However, this does not have to be the case. For the measuring signals of different sensors, different smoothing methods or the same smoothing method with different filter coefficients can be used. In the present case of a weighted moving average, the filter coefficients are the weighting factors of the respective measured values. This leads to unfiltered measured values which, for the nth breath of the distal flow sensor 48, could be as follows:

$$VT_{Serv_{Filt}}[n] = \frac{1}{64}\sum_{i=1}^{16} a_i \cdot VT_{Serv_{Filt}}[n-1]$$

with $a_i = \{1, 2, 3, 4, 5, 6, 7, 8, 8, 7, 6, 5, 4, 3, 2, 1\}$

In the example given, the measurements taken in the middle of the last 16 readings are most heavily weighted, with a linear increase from the most recent reading to the mean readings and a linear fall from the average readings to the oldest reading. Accordingly, the signal of the proximal sensor smoothed to determine a jump error can be as follows:

$$VT_{Prox_{Filt}}[n] = \frac{1}{64}\sum_{i=1}^{16} a_i \cdot VT_{Prox_{Filt}}[n-1]$$

where the weighting factors are the same.

The weighted smoothed average VTServfFilt is designated by the reference number 56 in FIG. 2 and the weighted smoothed mean VTproxFilt by the reference number 58.

The abscissa of the diagram of FIG. 2 denotes the time in minutes, the ordinate the volume in milliliters.

The change values which are important for the error detection of the respiration device according to the invention are particularly advantageously used as differences between the value of the current breath and the immediately preceding breath, whereby the smoothed values are preferably used to form the differences. The values of change VTserfDiff of the distal flow sensor 48 and $VTp_{ro}xDiff$ of the proximal flow sensor 44 can therefore be formed as follows:

$$VT_{Serv_{Diff}}[n] = VT_{Serv_{Filt}}[n] - VT_{Serv_{Filt}}[n-1]$$

$$VT_{Prox_{Diff}}[n] = VT_{Prox_{Filt}}[n] - VT_{Prox_{Filt}}[n-1]$$

Figure 3:
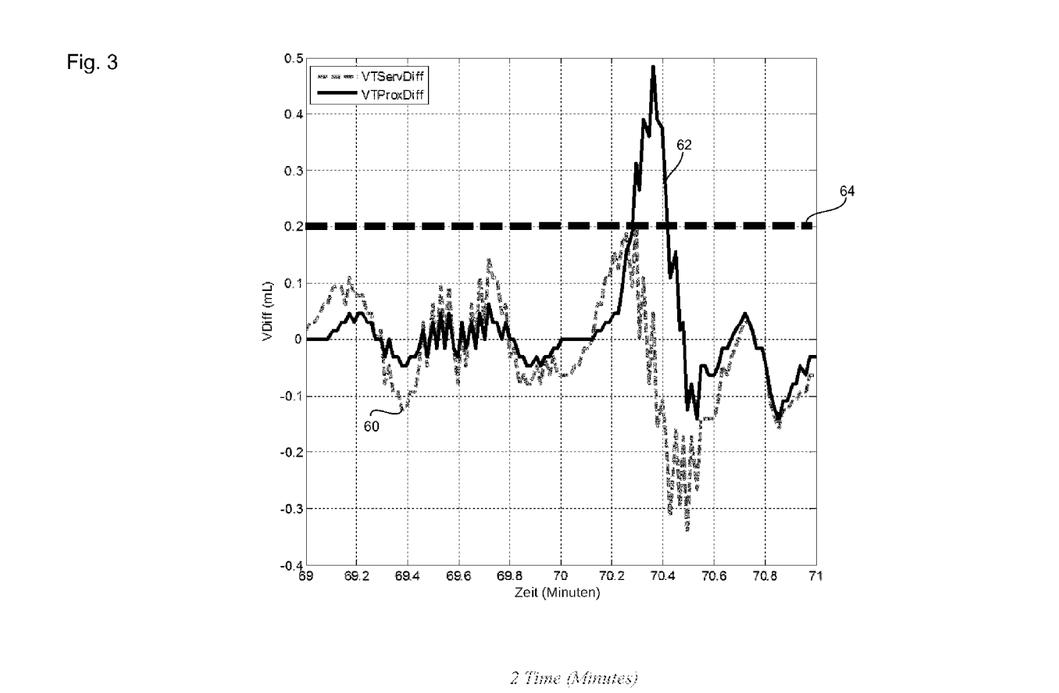
FIG. 3 shows a diagram with change values of the measuring signals of the distal and the proximal flow sensor.

These change values are shown over their time progression in FIG. 3. The change value of the distal flow sensor 48 is indicated by reference number 60, that of the proximal flow sensor 44 by reference number 62. The abscissa of the graph of FIG. 3 again show the time in minutes and the ordinate a volume, this time the volume of change, in milliliters.

In FIG. 3, denoted by reference number 64 is a threshold value which when exceeded by the change value 62 of the proximal flow sensor 44, causes the control device 18 to start the error detection method described in the introduction to the description. The start of the error detection process is coupled to exceeding the threshold value 64 so as not to spend unnecessary computing power on the error detection method of control device 18.

When at the k-th breath, the change value 62 of the proximal flow sensor 44 exceeds the threshold value 64 from the change value 62 of the proximal flow sensor 44, the change values of the proximal flow sensor 44 and distal flow sensor 48 of the immediately preceding (k−1)-th breath are respectively saved and used as reference values for a later comparison:

$$VT_{ServBezug} = VT_{ServFilt}[k-1]$$

$$VT_{ProxBezug} = VT_{ProxFilt}[k-1]$$

Then a summation of the change values begins:

$$VT_{ServSumme}[n] = VT_{ServSumme}[n-1] + VT_{ServDiff}[n]$$

$$VT_{ProxSumme}[n] = VT_{ProxSumme}[n-1] + VT_{ProxDiff}[n]$$

For each flow sensor 44 and 48, a sum value is thus formed, which for the n-th breath is the sum value of the immediately preceding (n−1)-th breath plus the current change value of the n-th breath.

In the illustrated configuration, the control device 18 recognizes a jump$_{error}$ when the ratio of the sum value of the proximal flow$_{sensor}$ 44 to the reference value $VT_{ProxVerazug\,of}$ the proximal flow$_{sensor}$ 44 exceeds a predetermined reference threshold, for example exceeds a reference threshold of 0.08, which means that the sum of change values of the proximal flow sensor since the beginning of the summation amounts to at least 8% of the reference value. The reference threshold may also have a value other than 8%, but in previous experiments 8% has proved to be a very good reference threshold.

As another condition, which may be added to that mentioned in the previous paragraph, is that the sum value of the distal flow sensor 48 may not vary by more than a further reference threshold—for example 10%—from the sum of the proximal flow sensor 44.

Alternatively, or in addition to the further condition mentioned in the preceding paragraph, the condition may occur that the current, preferably smoothed, value of the distal flow sensor 48 does not differ from its reference value by more than a greater reference threshold. This further reference threshold value may be, —for example, be between 1 and 5%. Experiments have pointed to the further reference threshold of 2% as effective.

Figure 6:
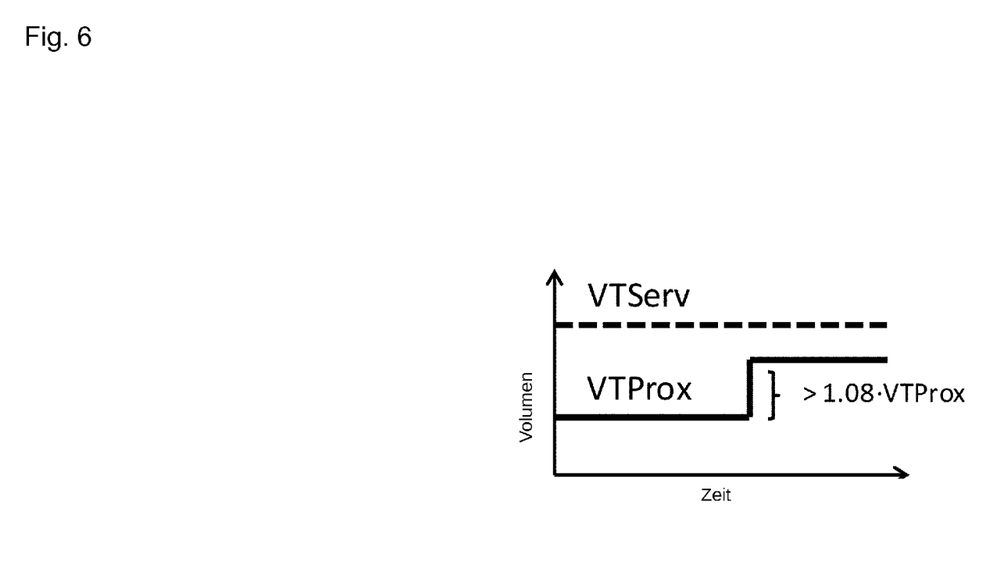
FIG. 6 shows a rough schematic diagram for error detection of a jump error.

The case of a jump error occurring at the proximal flow sensor 44 is shown thematically by way of example in FIG. 6.

Only when all predetermined conditions for reliable detection of a jump error are met, will the control device 18 detect the presence of a jump error and trigger a corresponding alarm, for example.

Smooth measured values are likewise used for the detection of a drift error which occurs creepingly, wherein preferably the smoothing of the measured values takes place over a larger number of past measured values than is the case with a jump error. For example, the smoothing can again take place by forming a weighted moving average, for example over the last 100 measured values:

$$VT_{ServFilt}[n] = \sum_{i=1}^{100} b_i \cdot VT_{ServFilt}[n-1]$$

$$VT_{ProxFilt}[n] = \sum_{i=1}^{100} b_i \cdot VT_{ProxFilt}[n-1]$$

The weighting coefficients bi are chosen so that the sum of all weighting coefficients is 1. Alternatively or additionally, the measured values can also be smoothed by a digital filter of a higher order, preferably at least of a fourth order.

Figure 4:
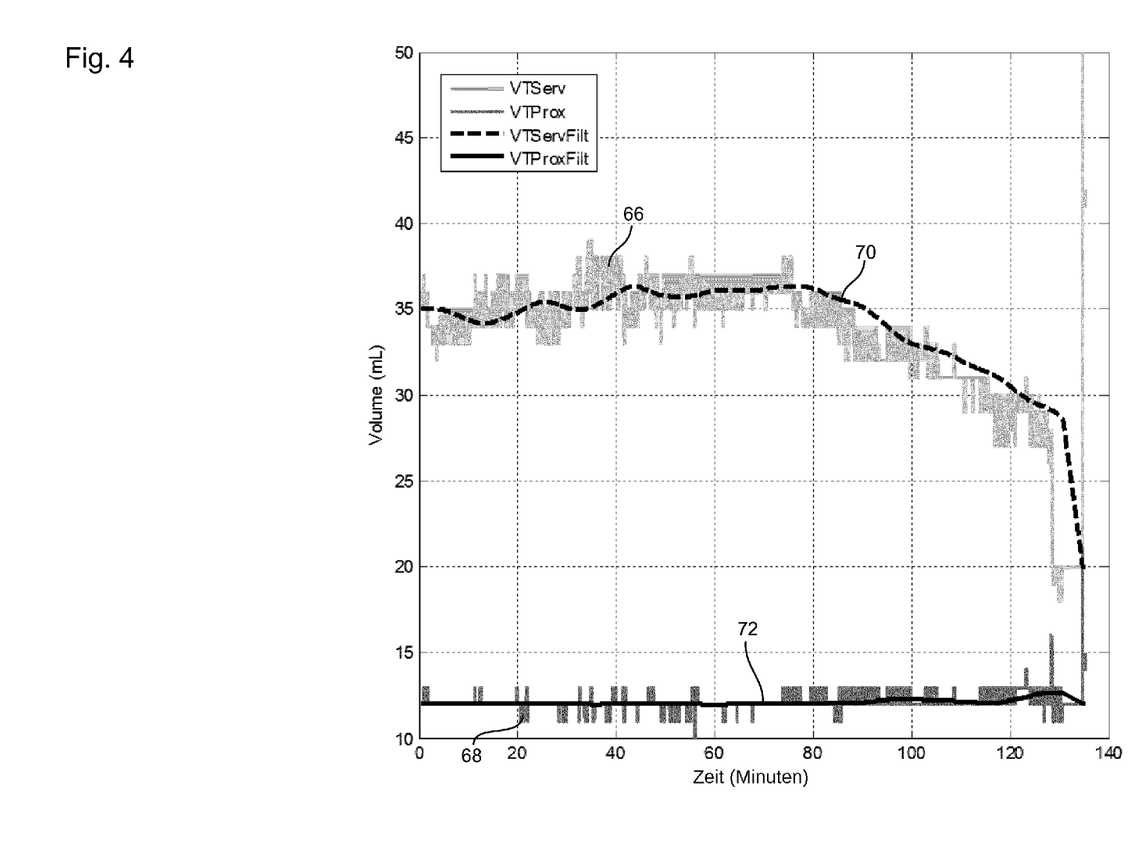
FIG. 4 shows another diagram with raw measurement signals and smoothed measurement signals of the distal and the proximal flow sensor.

In FIG. 4, the raw signals of the distal flow sensor 48 are denoted by reference number 66 and those of the proximal flow sensor 44 by reference number 68. The smoothed signal of the distal flow sensor 48 is denoted by reference number 70, the smoothed signal of the proximal flow sensor 44 by reference number 72.

The formation of the change values of the measurement signals 66 and 68 of the distal flow sensor 48 or proximal flow sensor 44 takes place as described above, namely by forming the difference between the smoothed measured value of the respective sensor for the current breath and that of the immediately preceding breath. So again:

$$VT_{ServDiff}[n] = VT_{ServFilt}[n] - VT_{ServFilt}[n-1]$$

$$VT_{ProxDiff}[n] = VT_{ProxFilt}[n] - VT_{ProxFilt}[n-1]$$

Figure 5:
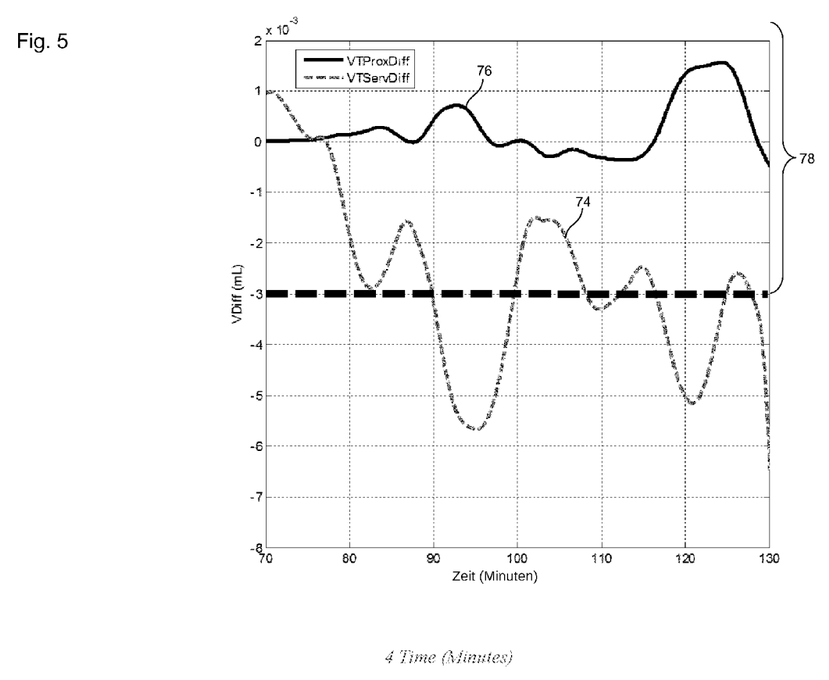
FIG. 5 shows a further diagram with change values of the measurement signals of the distal and the proximal flow sensor.

The change values of the measurement signals of the distal flow sensor 48 are designated in FIG. 5 by reference number 74, those of the proximal flow sensor 44 by reference number 76.

Again, error detection by the control device 18 will not begin until predetermined start conditions are met, such as when one of the change values leaves a tolerance band of 0 ml denoted 78 in FIG. 5 ml and/or if the change values have different signs. In FIG. 5, the upper edge of the tolerance band is not shown. It ranges from −3 to +3 ml. The change value tolerance band, the exit of which may be a start condition for the error detection by the control device 18, is preferably arranged symmetrically around the zero point. However, this does not have to be the case; depending on the application, it may also have different limits in terms of amount.

Then, when the predetermined start condition for the detection of a drift error is present, the control device 18 in turn starts, in the manner already described above, summing totals of the change values of each flow sensor 44 or 48:

$$VT_{ServSumme}[n] = VT_{ServSumme}[n-1] + VT_{ServDiff}[n]$$

$$VT_{ProxSumme}[n] = VT_{ProxSumme}[n-1] + VT_{ProxDiff}[n]$$

Likewise, the measured values of the proximal flow sensor 44 and distal flow sensor_48 of the breath which immediately preceded that breath in which the at least one start condition of an error detection was fulfilled are stored as reference values for later comparisons:

$$VT_{ServBezug} = VT_{ServFilt}[k-1]$$

$$VT_{ProxBezug} = VT_{ProxFilt}[k-1]$$

Here the error detection of a drift error does not differ from the error detection of a jump error.

The control device 18 in the present example identifies a drift error in the flow sensor arrangement when the ratio of the change sum value $VT_{Proxsum}$ [n] of the proximal flow sensor 44 to its reference $VT_{ProxRef}$ exceeds a predetermined reference threshold, and if the ratio of the change sum value $VT_{ServVsum}$ [n] of the distal flow sensor 48 to whose reference value $VT_{ServVRef}$ does not exceed a predetermined further reference threshold. The reference threshold value of the proximal flow sensor 44 for detecting a drift error may again be 8%, the further reference threshold may be, for example, 2%.

Similarly, in the present example, the control device 18 then identifies a drift error in the flow sensor arrangement when the ratio of the cumulative change value $VT_{ServVsum}$ [n] of the distal flow sensor 48 to its reference value $VT_{ServVRef}$ exceeds the predetermined reference threshold, and if, at the same time, the ratio of the proximate flow sensor change sum value 44 $VT_{ProXsum}$ [n] to whose reference value $VT_{ProXRef}$ does not exceed the predetermined further reference threshold. The example values for the reference threshold values given in the preceding paragraph apply.

Since the drift error can affect the proximal or distal flow sensor, the conditions for detecting the drift error are preferably symmetrical with respect to the two reference thresholds.

As an additional condition for detecting a drift error, it may be added that one of the two change sum values exceed a predetermined threshold change amount, for example, an amount of 2 ml.

Figure 7:
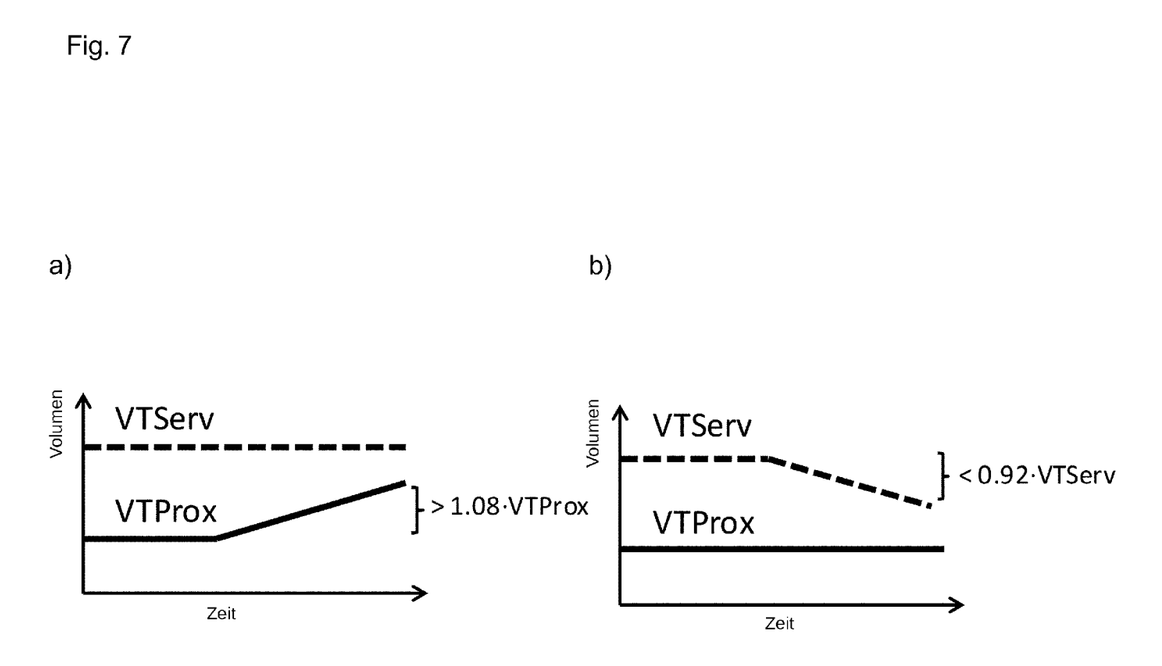
FIG. 7 shows rough schematic diagrams for error detection of a drift error.

The conditions for detecting a drift error on the basis of the change sum values are shown roughly schematically in FIGS. 7a and 7b. In the event of detection of a drift error, the control device 18 preferably triggers an alarm, but preferably continues to operate the flow sensor arrangement.

With the present ventilator 10 according to the invention, errors in the flow sensor arrangement can be detected more extensively and more accurately than previously.

The invention claimed is:

1. A ventilation device for artificial respiration with
   a breathing gas source,
   a ventilation line arrangement extending between the breathing gas source and a patient-side proximal end,
   a valve assembly comprising an inspiratory valve and an expiratory valve,
   a flow sensor arrangement for the quantitative detection of a gas flow in the ventilation line arrangement comprising a distal flow sensor located farther from the patient end of the ventilation line arrangement and a proximal flow sensor located closer to the patient end of the ventilation line arrangement, and
   a control device at least for processing measurement signals of the flow sensor arrangement, wherein the control device is adapted to error detection based on measurement signals of at least one of the distal and the proximal flow sensor,
   wherein the control device is adapted to detect an error of the flow sensor arrangement based on a comparison of a change value of a measurement signal of one flow sensor out of the proximal flow sensor and the distal flow sensor with at least one of
   a change value of a measurement signal of the respective other flow sensor out of the proximal flow sensor and the distal flow sensor and
   a measuring signal of the one flow sensor,
   wherein the control device is adapted to detect a jump error of the flow sensor arrangement when
   a ratio of a sum value of consecutively occurring change values of the measurement signal of the proximal flow sensor to a first reference variable exceeds a predetermined reference threshold value, and
   a ratio of a sum value of consecutively occurring change values of the measurement signal of the distal flow sensor to a second reference variable falls below a predetermined reference threshold value.

2. The ventilation device according to claim 1,
   wherein the control device is adapted to detect an error of the flow sensor arrangement when the change value of the measurement signal of the one flow sensor out of the distal and proximal flow sensor has an opposite direction of change than the change value of the respective other flow sensor.

3. The ventilation device according to claim 1, wherein at least one of the first and the second reference variable is a measured signal value of the proximal flow sensor.

4. The ventilation device according to claim 1,
   wherein the proximal and the distal flow sensor each provide one measured value per breath, which represents the gas flow associated with this breath.

5. The ventilation device according to claim 1,
   wherein the proximal flow sensor is a differential pressure sensor.

6. The ventilation device according to claim 1,
   wherein the control device is adapted to emit an alarm when it detects an error.

7. The ventilation device according to claim 1,
   wherein the control device is adapted to detect an error of the flow sensor arrangement when
   a ratio of a sum value of immediately successive change values of the measurement signal of the proximal flow sensor to a first reference variable exceeds a predetermined reference threshold value, and
   a ratio of a sum value of immediately successive change values of the measurement signal of the distal flow sensor to a second reference variable falls below a predetermined reference threshold value.

8. The ventilation device according to claim 3,
   wherein at least one of the first and the second reference variable is a measured signal value of the proximal flow sensor at or immediately before the beginning of the summation of the change values.

9. The ventilation device according to claim 1,
   wherein the control device is adapted to detect an error of the flow sensor arrangement when
   a ratio of a sum value of immediately successive change values of the measurement signal of the proximal flow sensor to a third reference variable exceeds a predetermined reference threshold value, and
   a ratio of a sum value of immediately successive change values of the measurement signal of the distal flow sensor to a fourth reference variable falls below a predetermined reference threshold value,
   or to detect an error in the flow sensor arrangement when
   a ratio of a sum value of immediately successive change values of the measurement signal of the proximal flow sensor to a fifth reference value falls below a predetermined reference threshold and
   a ratio of a sum value of immediately successive change values of the measurement signal of the distal flow sensor to a sixth reference value exceeds a predetermined reference threshold value.

10. The ventilation device according to claim 1, wherein the control device is adapted to start adding change values when at least one of the measurement signal value and the change value of the proximal flow sensor has exceeded a predetermined signal threshold.

11. The ventilation device according to claim 10,
    wherein the control device is adapted to process the measuring signals of the proximal and the distal flow sensor on by-breath basis, wherein when the measured signal value of the proximal flow sensor exceeds the predetermined signal threshold at a threshold breath, at least one of the first and second reference variable is the measurement signal value of the proximal flow sensor, which is associated with the breath immediately preceding the threshold breath.

12. The ventilation device according to claim 1,
    wherein the control device is adapted to smooth the measurement signals of the flow sensors by filtering or by a digital filter with a higher order than 1.

13. The ventilation device according to claim 12, further configured to determine the change values on the basis of the smoothed measurement signals.

14. The ventilation device according to claim 1,
wherein the proximal and the distal flow sensor each provide exactly one measured value per breath, which represents the gas flow associated with this breath.

15. The ventilation device according to claim 1,
wherein the control device is adapted to emit an alarm when it detects an error, and continues to process measurement signals from the proximal flow sensor.

16. The ventilation device according to claim 1,
wherein the control device is adapted to smooth the measurement signals of the flow sensors by moving averaging, or by a digital filter with a higher order than 1.

17. The ventilation device according to claim 16, further configured to determine the change values on the basis of the smoothed measurement signals.

18. The ventilation device according to claim 1,
wherein the control device is adapted to smooth the measurement signals of the flow sensors by filtering, or by a digital filter with a higher order than 1.

19. The ventilation device according to claim 18, further configured to determine the change values on the basis of the smoothed measurement signals.

20. The ventilation device according to claim 1,
wherein the control device is adapted to smooth the measurement signals of the flow sensors by forming a sliding weighted average, or by a digital filter with a higher order than 2.

21. The ventilation device according to claim 20, further configured to determine the change values on the basis of the smoothed measurement signals.

22. The ventilation device according to claim 1,
wherein the control device is adapted to smooth the measurement signals of the flow sensors by forming a sliding weighted average, or by a digital filter with a fourth-order digital filter.

23. The ventilation device according to claim 22, further configured to determine the change values on the basis of the smoothed measurement signals.

24. The ventilation device according to claim 1,
wherein the control device is adapted to detect an error of the flow sensor arrangement when
a ratio of a sum value of consecutively occurring change values of the measurement signal of the proximal flow sensor to a third reference variable exceeds a predetermined reference threshold value, and
a ratio of a sum value of successively occurring change values of the measurement signal of the distal flow sensor to a fourth reference variable falls below a predetermined reference threshold value,
or to detect an error in the flow sensor arrangement when
a ratio of a sum value of consecutively occurring change values of the measurement signal of the proximal flow sensor to a fifth reference value falls below a predetermined reference threshold and
a ratio of a sum value of consecutively occurring change values of the measurement signal of the distal flow sensor to a sixth reference value exceeds a predetermined reference threshold value.

25. The ventilation device according to claim 24,
wherein the control device is adapted to detect an error of the flow sensor arrangement, only if in addition, at least one of
the sum value of consecutively occurring change values of the measurement signal of the proximal flow sensor exceeds a predetermined first sum threshold value, and
the sum value of consecutively occurring change values of the measurement signal of the distal flow sensor exceeds a predetermined second sum threshold value.

26. The ventilation device according to claim 24,
wherein at least one of the third and the fifth reference variable is a measurement signal value of the proximal flow sensor.

27. The ventilation device according to claim 24,
wherein at least one of the fourth and the sixth reference value is a measurement signal value of the distal flow sensor.

28. The ventilation device according to claim 24,
wherein the summation of change values to form summation values begins when the absolute value of the change value of the measurement signal of at least one of the proximal and the distal flow sensor exceeds a predetermined absolute value threshold value.

29. The ventilation device according to claim 24,
wherein the control device is adapted to detect an error of the flow sensor arrangement, only if in addition, at least one of
the sum value of immediately successive change values of the measurement signal of the proximal flow sensor exceeds a predetermined first sum threshold value, and
the sum value of immediately successive change values of the measurement signal of the distal flow sensor exceeds a predetermined second sum threshold value.

30. The ventilation device according to claim 24,
wherein at least one of the third and the fifth reference variable is a measurement signal value of the proximal flow sensor at or immediately before the beginning of the summation of the change values.

31. The ventilation device according to claim 24,
wherein at least one of the fourth and the sixth reference value is a measurement signal value of the distal flow sensor at or immediately before the beginning of the summation of the change values.

* * * * *